(12) United States Patent
Chaudhuri et al.

(10) Patent No.: US 10,301,373 B2
(45) Date of Patent: May 28, 2019

(54) **PROCESS FOR ENHANCED PRODUCTION OF RECOMBINANT HUMAN SERUM ALBUMIN IN *E. COLI* THROUGH CHAPERONE ASSISTANCE**

(71) Applicant: Indian Institute of Technology, Delhi, New Delhi (IN)

(72) Inventors: Tapan Kumar Chaudhuri, New Delhi (IN); Ashima Sharma, New Delhi (IN)

(73) Assignee: Indian Institute of Technology, Delhi, New Delhi (IN)

( * ) Notice: Subject to any disclaimer, the term of this patent is extended or adjusted under 35 U.S.C. 154(b) by 204 days.

(21) Appl. No.: 15/588,379

(22) Filed: May 5, 2017

(65) Prior Publication Data
US 2018/0186858 A1    Jul. 5, 2018

(30) Foreign Application Priority Data

Dec. 30, 2016    (IN) .............................. 201611045154

(51) Int. Cl.
| | | |
|---|---|---|
| *C12P 21/00* | (2006.01) | |
| *C07K 14/765* | (2006.01) | |
| *A01N 63/00* | (2006.01) | |
| *C12N 15/70* | (2006.01) | |

(52) U.S. Cl.
CPC ............ *C07K 14/765* (2013.01); *C12P 21/00* (2013.01)

(58) Field of Classification Search
CPC combination set(s) only.
See application file for complete search history.

(56) References Cited

PUBLICATIONS

Shivcharan Prasad et al (Effect of Chemical Chaperones in Improving the Solubility of Recombinant Proteins in *Escherichia coli*. Applied and Environmental Microbiology, Jul. 2011, p. 4603-4609) (Year: 2011).*
Boldt, "Use of albumin: an update," *British Journal of Anaesthesia* 104(3):276-284, 2010.
Chen et al., "Human serum albumin from recombinant DNA technology: Challenges and strategies," *Biochimica et Biophysica Acta* 1830:5515-5525, 2013.
Ghafari et al., "Expression of recombinant human serum albumin in *E. coli* (BL21)," *New Cellular and Molecular Biotechnology Journal* 3(9):61-66, 2013 (with English Abstract, 7 pages).
Kobayashi, "Summary of recombinant human serum albumin development," *Biologicals* 34:55-59, 2006.
Latta et al., "Synthesis and Purification of Mature Human Serum Albumin from *E. coli*," *Biotechnology* 5:1309-1314, 1987.
Lawn et al., "The sequence of human serum albumin cDNA and its expression in *E. coli*," *Nucleic Acids Research* 9(22):6103-6114, 1981.
Rosano et al., "Recombinant protein expression in *Escherichia coli*: advances and challenges," *Frontiers in Microbiology* 5: 2014, 17 pages.
Tripathi et al., "High Yield Production of Heterologous Proteins with *Escherichia coli*," *Defence Science Journal* 59(2):137-146, 2009.

\* cited by examiner

*Primary Examiner* — Kagnew H Gebreyesus
(74) *Attorney, Agent, or Firm* — Seed IP Law Group LLP

(57) ABSTRACT

The present disclosure provides a process for improved production and extraction of recombinant human serum albumin (rHSA) using *E. coli* as a host system. The process of the instant disclosure provides enhanced recovery of soluble and functional rHSA over conventional known methods.

7 Claims, 3 Drawing Sheets
Specification includes a Sequence Listing.

PROCESS FOR ENHANCED PRODUCTION OF RECOMBINANT HUMAN SERUM ALBUMIN IN *E. COLI* THROUGH CHAPERONE ASSISTANCE

STATEMENT REGARDING SEQUENCE LISTING

The Sequence Listing associated with this application is provided in text format in lieu of a paper copy, and is hereby incorporated by reference into the specification. The name of the text file containing the Sequence Listing is 480337_401_SEQUENCE_LISTING.txt. The text file is 776 bytes, was created on May 3, 2017, and is being submitted electronically via EFS-Web.

FIELD OF INVENTION

The present disclosure relates to the field of molecular biology. In particular, the present disclosure relates to the further improvement and enhancement of the expression and isolation of soluble and functional recombinant human serum albumin in E co/i.

BACKGROUND OF THE INVENTION

Human serum albumin (HSA) is the most abundant protein of human plasma and performs wide range of functions such as maintaining the plasma oncotic pressure, functioning as an antioxidant, carrying out functions as a universal transport and depot protein with extraordinary ligand binding capacity and modulating fluid distribution; it also displays various important enzymatic and anti-inflammatory activities (Boldt J, British Journal of Anaesthesia 2010; 104(3):276-84). HSA is a valuable biomarker of several diseases. Moreover, clinically HSA has been employed to treat several diseases including hypovolemia, shock, burns, surgical blood loss, trauma, hemorrhage, etc. It is also utilized as an excipient for vaccines, supplement in cell culture medium, carrier of oxygen and in various others biotechnological applications (Kobayashi, Biologicals 34 (2006); 55-59).

Its wide applications and immense therapeutic potential, makes HSA a protein that is highly in demand, and it is estimated that the annual world need for this protein exceeds 500 tons. Currently, HSA is obtained primarily from the fractionation of collected human blood that is a limited and an unsafe source as there exists the risk of it being contaminated by various blood derived pathogens like HIV, hepatitis and the like.

To eliminate the potential risk of contamination, there is an indispensable need to develop non-animal-derived alternatives and low cost methods to obtain large quantities of pathogen free recombinant HSA as a primary substitute for the plasma-derived form (Chen et. al, Biochimica et Biophysica Acta 1830 (2013): 5515-5525).

HSA is a 66.5 kDa monomeric, single chain, non-glycosylated, heart shaped protein made up of three homologous domains containing 17 disulfide bonds and one free sulfhydryl group (Kobayashi, Biologicals 34 (2006): 55-59). The non-glycosylated and single chain polypeptide features of HSA make it less complex than the other blood extracted proteins like plasminogen activator and clotting factors, and has encouraged various research groups to carry out number of attempts for the production of HSA. Over the past couple of decades extensive research is going in the direction, but till yet no host system has been proven to be ideal enough when, rHSA production is the concerned issue, because of their respective limitations. Surprisingly, one of the branches had remained very less explored i.e. rHSA production using *E. coli* as a host system.

*E. coli* is one of the most convenient host systems that has contributed in the production of more than 30% approved recombinant pharmaceuticals by FDA (major examples include human insulin, plasminogen activator, growth hormone etc) (Ceccarelli et. al, Frontiers in microbiology (2014); 5 (172)). *E. coli* derived products have more economical potential as fermentation processes are more economical compared to other expression hosts as it grows rapidly and reach high cell densities using inexpensive and simple substrates (Tripathi et al., Defence Science Journal (2009); 59 (2): 137-146). However, it has not been exploited for rHSA production.

Till date *E. coli* has not been exploited for the production of recombinant HSA for therapeutic usage. This is due to the fact that a majority of the recombinantly expressed HSA proteins in *E. coli* host system form aggregates (more than 90% of the expressed rHSA) leading to the formation of inclusion body as previously reported (Lawn, Nucleic Acids Res. 1981; 9:6103-6114; Latta, BioTechnol. 1987; 5: 1309-1314). An attempt to express rHSA in the periplamsic space of the *E. coli* host system has also been carried out recently (Ghafari et. al, New cellular biotechnology journal (2013); 3 (9)) but it explores only a preliminary narrow era with the prime goal to check the status of expression of rHSA in a periplasmic space and reveals no more in addition to that.

A recent process developed by the inventors results in the recovery of 60% of the total expressed rHSA in the soluble fraction. (Patent application filed no. 201611027096, entitled—"Process for production, and isolation of recombinant human serum albumin in *E. coli*"). The process was based on the modulation of the cellular growth parameters followed by osmolytic assistance at a crucial cell lysis step of rHSA preparation from *E. coli* host system. However, a limitation of the method is that some fraction of proteins obtained from the soluble fraction is not functionally active and display lower levels of activity as compared to ideal situations.

SUMMARY OF THE INVENTION

In an aspect of the present disclosure, there is provided a process for production of soluble recombinant human serum albumin (rHSA) comprising:

(a) obtaining recombinant *E. coli* host cells co-expressing rHSA and Trigger factor (molecular chaperone);

(b) culturing said recombinant *E. coli* host cells in an auto-induction culture medium at a temperature in the range of 30-40° C. and for a time period of 6-12 hours until said culture reaches $OD_{600}$ in the range of 0.2 to 0.5;

(c) adding L-Arabinose (inducer of trigger factor) to the above culture medium at a concentration in the range of 0.3 to 0.6 mg/ml;

(d) culturing said recombinant *E. coli* host cells in the above culture medium induced with L-Arabinose at a temperature in the range of 30-40° C. until said culture reaches $OD_{600}$ in the range of 0.6-1.0;

(e) culturing the said recombinant host cells in the same culture medium at a temperature in the range of 10-20° C. for a period of 8 to 10 hours;

(f) obtaining recombinant *E. coli* host cells; and
(g) extracting rHSA from the recombinant *E. coli* host cells, wherein said process results in 20-30% increase in functionally active soluble rHSA protein, compared to soluble rHSA levels obtained without expression of the Trigger factor under said conditions.

In an aspect of the present disclosure, there is provided a process for production of rHSA protein as described herein, wherein the process of extracting rHSA comprises:
(a) obtaining recombinant *E. coli* host cells as described herein;
(b) adding to the recombinant *E. coli* host cells, lysis buffer comprising osmolytes in the range of 0.1 to 1.0 M and incubating for 15-30 mins.
(c) sonicating the recombinant *E. coli* host cells to obtain a cell lysate;
(d) centrifuging said cell lysate to obtain supernatant fraction;
(e) extracting rHSA from the supernatant fraction to obtain soluble rHSA.

In an aspect of the present disclosure, there is provided a method of extracting recombinant human serum albumin (rHSA) comprising:
(a) obtaining recombinant *E. coli* Origami2 (DE3) cells comprising a plasmid expressing rHSA and a plasmid pTf16 expressing Trigger factor (molecular chaperone);
(b) culturing said recombinant *E. coli* Origami2 (DE3) host cells in ZY medium comprising ampicillin and chloramphenicol, at a temperature in the range of 30-40° C. and for a time period of 6-12 hours until the culture reaches an $OD_{600}$ in the range of 0.2 to 0.5;
(c) adding L-Arabinose (inducer of trigger factor) at a concentration in the range of 0.3 to 0.6 mg/ml;
(d) culturing said recombinant *E. coli* Origami2 (DE3) cells in the above culture medium at a temperature in the range of 30-40° C. until the culture reaches an $OD_{600}$ in the range of 0.6-1.0;
(e) culturing the said recombinant *E. coli* Origami2 (DE3) host cells in the same culture medium at a temperature in the range of 10-20° C. for a period of 8 to 10 hours;
(f) obtaining recombinant *E. coli* Origami2 (DE3) cells;
(g) adding lysis buffer comprising trehalose (osmolyte) in the range of 0.5 to 1.0 M and incubating for 15-30 min;
(h) sonicating the recombinant *E. coli* Origami2 (DE3) cells to obtain cell lysate;
(i) centrifuging said cell lysate to obtain supernatant fraction;
(j) extracting rHSA from the supernatant fraction to obtain soluble rHSA,
wherein said process results in 1.5-2.0 fold increase in rHSA soluble protein levels and 20-30% increase in functionally active soluble rHSA protein, compared to soluble rHSA levels obtained without expression of molecular chaperone under said conditions.

BRIEF DESCRIPTION OF THE ACCOMPANYING DRAWINGS

DETAILED DESCRIPTION OF THE INVENTION

Figure 1A:
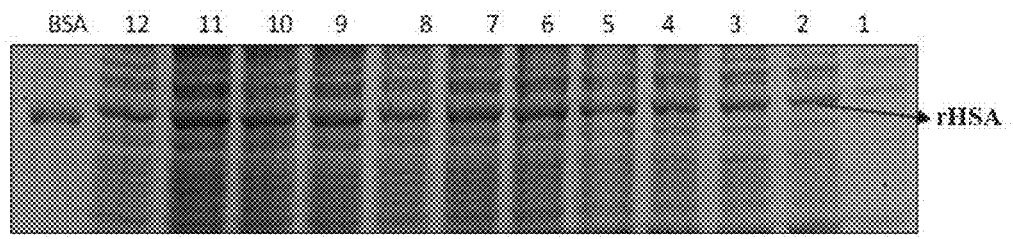
FIGS. 1a-1c show the expression levels of rHSA protein in the presence and absence of Trigger Factor (molecular chaperone), in accordance with the present disclosure.

Those skilled in the art will be aware that the present disclosure is subject to variations and modifications other than those specifically described. It is to be understood that the present disclosure includes all such variations and modifications. The disclosure also includes all such steps, features, compositions and compounds referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

The present disclosure provides a method of harnessing the scalable, and cost effective power of *E. coli* system for expression of recombinant proteins, particularly recombinant human serum albumin (rHSA). The present disclosure provides a method of expression of high levels of soluble and functional rHSA. This is achieved by using a molecular chaperone—Trigger Factor—which assists the folding of the rHSA protein, thus helping to obtain higher levels of soluble and functional rHSA protein from heterologous expression in *E. coli* cells.

Sequences:

SEQ ID NO: 1 depicts the forward primer to amplify HSA.
AAAGCTAGCATGGATGCACACAAGAGTG SEQ ID NO: 2 depicts the reverse primer to amplify HSA.
GGACTCGAGTAAGCCTAAGGCAGC In an embodiment of the present disclosure, there is provided a process for production of soluble recombinant human serum albumin (rHSA) comprising:
(a) obtaining recombinant *E. coli* host cells co-expressing rHSA and Trigger factor (molecular chaperone);
(b) culturing said recombinant *E. coli* host cells in an auto-induction culture medium at a temperature in the range of 30-40° C. and for a time period of 6-12 hours until said culture reaches $OD_{600}$ in the range of 0.2 to 0.5;
(c) adding L-Arabinose (inducer of trigger factor) to the above culture medium at a concentration in the range of 0.3 to 0.6 mg/ml;
(d) culturing said recombinant *E. coli* host cells in the above culture medium induced with L-Arabinose at a temperature in the range of 30-40° C. until said culture reaches $OD_{600}$ in the range of 0.6-1.0;
(e) culturing the said recombinant host cells in the same culture medium at a temperature in the range of 10-20° C. for a period of 8 to 10 hours;
(f) obtaining recombinant *E. coli* host cells; and
(g) extracting rHSA from the recombinant *E. coli* host cells, wherein said process results in 20-30% increase in functionally active soluble rHSA protein, compared to active soluble rHSA levels obtained without the expression of the Trigger factor under said conditions.

In an aspect of the present disclosure, there is provided a process for production of rHSA protein as described herein, wherein the process of extracting rHSA comprises:
(a) obtaining recombinant *E. coli* host cells as described herein;
(b) adding to the host cells lysis buffer comprising osmolytes in the range of 0.1 to 1.0 M and incubating for 15-30 mins.
(c) sonicating the recombinant *E. coli* host cells to obtain a cell lysate;
(d) centrifuging said cell lysate to obtain supernatant fraction; and
(e) extracting rHSA from the supernatant fraction to obtain soluble rHSA.

In an embodiment of the present disclosure, there is provided the process described herein, wherein the molecular chaperone is selected from the group consisting of GroEL, GroES, Trigger Factor, PDI, Bip.

In an embodiment of the present disclosure, there is provided the process described herein, wherein the molecular chaperone is Trigger Factor.

In an embodiment of the present disclosure, there is provided the process described herein, wherein Trigger Factor is induced by 0.3-0.6 mg/ml of L-Arabinose.

In an embodiment of the present disclosure, there is provided the process described herein, wherein Trigger Factor is induced by 0.4-0.6 mg/ml of L-Arabinose.

In an embodiment of the present disclosure, there is provided the process described herein, wherein after the addition of L-Arabinose at a concentration of 0.3-0.6 mg/ml, the recombinant *E. coli* cells are cultured at a temperature in the range of 30-40° C. until $OD_{600}$ is in the range of 0.6-1.0.

In an embodiment of the present disclosure, there is provided the process described herein, wherein after the addition of L-Arabinose at a concentration of 0.3-0.6 mg/ml, the recombinant cells are cultured at a temperature in the range of 35-37° C. until $OD_{600}$ is in the range of 0.6-1.0.

In an embodiment of the present disclosure, there is provided the process described herein, wherein after the addition of L-Arabinose at a concentration of 0.4-0.6 mg/ml, the recombinant cells are cultured at a temperature in the range of 30-40° C. until $OD_{600}$ is in the range of 0.6-1.0.

In an embodiment of the present disclosure, there is provided the process as described herein, wherein culturing said recombinant host cells in an auto-induction culture medium is carried out at a temperature in the range of 15-20° C. for a time period in the range of 6-12 hours.

In an embodiment of the present disclosure, there is provided the process as described herein, wherein culturing said recombinant host cells in an auto-induction culture medium is carried out at a temperature in the range of 10-20° C. for a time period in the range of 8-12 hours.

In an embodiment of the present disclosure, there is provided the process as described herein, wherein culturing said recombinant host cells in an auto-induction culture medium is carried out at a temperature in the range of 15-20° C. for a time period in the range of 8-12 hours.

In an embodiment of the present disclosure, there is provided a process as described herein, wherein said recombinant host cells optical density as measured at a wavelength of 600 nm ($OD_{600}$) in said culture medium prior to culturing at 10-20° C. is in the range of 0.6-1.

In an embodiment of the present disclosure, there is provided a process as described herein, wherein said recombinant host cells optical density as measured at a wavelength of 600 nm ($OD_{600}$) in said culture medium prior to culturing at 15-20° C. is in the range of 0.6-1.

In an embodiment of the present disclosure, there is provided a process as described herein, wherein said recombinant host cell is *E. coli* Origami2 (DE3).

In an embodiment of the present disclosure, there is provided a process as described herein, wherein said recombinant *E. coli* Origami2 (DE3) host cells, are capable of expressing recombinant human serum albumin (rHSA).

In an embodiment of the present disclosure, there is provided a process as described herein, wherein said recombinant *E. coli* Origami2 (DE3) host cells, are co-expressing recombinant human serum albumin (rHSA) and least one molecular chaperone selected from the group consisting of GroEL, GroES, Trigger Factor, Bip, PDI In an embodiment of the present disclosure, there is provided a process as described herein, wherein said recombinant *E. coli* Origami2 (DE3) host cells, are co-expressing recombinant human serum albumin (rHSA) and a plasmid Tf16 expressing the Trigger Factor (molecular chaperone).

In an embodiment of the present disclosure, there is provided a process for expression of soluble recombinant human serum albumin (rHSA) comprising:
(a) obtaining recombinant *E. coli* Origami2 (DE3) host cells co-expressing rHSA and a plasmid pTf16 expressing Trigger factor (molecular chaperone);
(b) culturing said recombinant *E. coli* Origami2 (DE3) host cells in an auto-induction culture medium at a temperature in the range of 30-40° C. for a time period in the range of 6-12 hours, (c) adding L-Arabinose (inducer of trigger factor) at a concentration in the range of 0.3-0.6 mg/ml,
(d) culturing said recombinant E. coli Origami2 (DE3) host cells the above culture medium until $OD_{600}$ is in the range of 0.6-1.0 at a temperature in the range of 30-40° C.;
(e) culturing said recombinant E. coli Origami2 (DE3) host cells in the same induction medium at a temperature in the range of 10-20° C. for a period of 8-10 hours, wherein said process results in expression of in the expression of rHSA whereby said process results in 20-30% increase in functionally active soluble protein compared to soluble rHSA levels obtained without expression of molecular chaperone under said conditions.

In an embodiment of the present disclosure, there is provided a method of extraction of functionally active soluble rHSA as described herein, wherein said osmolyte is selected from the group consisting of trehalose, sucrose, sorbitol, mannitol, sodium citrate, betaine, L-proline, and combinations thereof.

In an embodiment of the present disclosure, there is provided a method of extraction of functionally active soluble rHSA as described herein, wherein said osmolyte is trehalose.

In an embodiment of the present disclosure, there is provided a method of extraction of functionally active rHSA as described herein, wherein osmolyte concentration is in the range of 0.5-1M.

In an embodiment of the present disclosure, there is provided a method of extraction of functionally active soluble rHSA as described herein, wherein rHSA activity of isolated rHSA is about 2 fold more than rHSA activity of rHSA isolated in the absence of osmolytes.

In an embodiment of the present disclosure, there is provided a method of extraction of functionally active soluble rHSA as described herein,
(a) obtaining recombinant E. coli Origami2 (DE3) host cells co-expressing rHSA and a plasmid pTf16 expressing Trigger factor (molecular chaperone);
(b) culturing said recombinant E. coli Origami2 (DE3) host cells in an auto-induction culture medium at a temperature in the range of 30-40° C. for a time period in the range of 6-12 hours,
(c) adding L-Arabinose (inducer of trigger factor) at a concentration in the range of 0.3-0.6 mg/ml,
(d) culturing said recombinant E. coli Origami2 (DE3) host cells the above culture medium until $OD_{600}$ is in the range of 0.6-1.0 at a temperature in the range of 30-40° C.;
(e) culturing said recombinant E. coli Origami2 (DE3) host cells in the same induction medium at a temperature in the range of 10-20° C. for a period of 8-10 hours,
wherein said process results in expression of in the expression of rHSA whereby said process results in 20-30% increase in functionally active soluble protein compared to soluble rHSA levels obtained without expression of molecular chaperone under said conditions.

In an embodiment of the present disclosure, there is provided a method of extraction of functionally active soluble rHSA comprising the step of co-expression of rHSA and Tigger Factor (molecular chaperone) as described herein, wherein Trigger Factor is induced by 0.3-0.6 mg/ml of L-Arabinose.

In an embodiment of the present disclosure, there is provided a method of extraction of functional rHSA comprising the step of co-expression of rHSA and Tigger Factor (molecular chaperone) as described herein, wherein Trigger Factor is induced by 0.4-0.6 mg/ml of L-Arabinose.

In an embodiment of the present disclosure, there is provided a method of extraction of functional rHSA comprising the step of co-expression of rHSA and Tigger Factor (molecular chaperone) as described herein, wherein after the addition of L-Arabinose at a concentration of 0.3-0.6 mg/ml, the recombinant cells are cultured at a temperature in the range of 30-40° C. until $OD_{600}$ is in the range of 0.6-1.0.

In an embodiment of the present disclosure, there is provided a method of extraction of functionally active soluble rHSA comprising the step of co-expression of rHSA and Tigger Factor (molecular chaperone) as described herein, wherein after the addition of L-Arabinose at a concentration of 0.3-0.6 mg/ml, the recombinant cells are cultured at a temperature in the range of 35-37° C. until $OD_{600}$ is in the range of 0.6-1.0.

In an embodiment of the present disclosure, there is provided a method of extraction of functionally active soluble rHSA comprising the step of co-expression of rHSA and Tigger Factor (molecular chaperone) as described herein, wherein after the addition of L-Arabinose at a concentration of 0.4-0.6 mg/ml, the recombinant cells are cultured at a temperature in the range of 30-40° C. until $OD_{600}$ is in the range of 0.6-1.0.

In an embodiment of the present disclosure, there is provided a method of extraction of functionally active soluble rHSA comprising the step of co-expression of rHSA and Tigger Factor (molecular chaperone) as described herein, wherein culturing said recombinant host cells in an auto-induction culture medium is carried out at a temperature in the range of 15-20° C. for a time period in the range of 6-12 hours.

In an embodiment of the present disclosure, there is provided a method of extraction of functionally active soluble rHSA comprising the step of co-expression of rHSA and Tigger Factor (molecular chaperone) as described herein, wherein culturing said recombinant host cells in an auto-induction culture medium is carried out at a temperature in the range of 10-20° C. for a time period in the range of 8-12 hours.

In an embodiment of the present disclosure, there is provided a method of extraction of functional rHSA comprising the step of co-expression of rHSA and Tigger Factor (molecular chaperone) as described herein, wherein culturing said recombinant host cells in an auto-induction culture medium is carried out at a temperature in the range of 15-20° C. for a time period in the range of 8-12 hours.

In an embodiment of the present disclosure, there is provided a method of extraction of functional rHSA comprising the step of co-expression of rHSA and Tigger Factor (molecular chaperone) as described herein, wherein said recombinant host cells optical density as measured at a wavelength of 600 nm ($OD_{600}$) in said culture medium prior to culturing at 10-20° C. is in the range of 0.6-1.

In an embodiment of the present disclosure, there is provided a method of extraction of functional rHSA comprising the step of co-expression of rHSA and Tigger Factor (molecular chaperone) as described herein, wherein said recombinant host cells optical density as measured at a wavelength of 600 nm ($OD_{600}$) in said culture medium prior to culturing at 15-20° C. is in the range of 0.6-1.

In an embodiment of the present disclosure, there is provided a method of extraction of functional rHSA comprising the step of rHSA expression as described herein, wherein said recombinant host cell is or E. coli Origami2.

In an embodiment of the present disclosure, there is provided a method of extraction of recombinant human serum albumin (rHSA) comprising:

(a) obtaining recombinant E. coli Origami (DE3) cells comprising a plasmid co-expressing rHSA and a plasmid pTf16 expressing Trigger factor (molecular chaperone);
(b) culturing said recombinant E. coli host cells in an auto-induction culture medium at a temperature in the range of 30-40° C. and for a time period of 6-12 hours until OD 600 is in the range of 0.2 to 0.5;
(c) adding L-Arabinose (inducer of trigger factor) at a concentration in the range of 0.4 to 0.6 mg/ml;
(d) culturing said recombinant host cells in the above culture medium until $OD_{600}$ is in the range of 0.6-1.0 at a temperature in the range of 30-40° C.;
(e) culturing the said recombinant host cells in the same induction medium at a temperature in the range of 10-20° C. for a period of 8 to 10 hours; and
(f) extracting rHSA in the presence of trehalose, wherein the concentration of trehalose is in the range of 0.5M-1M, wherein said process results in 1.5-2.0 fold increase in rHSA soluble protein levels and 20-30% increase in functionally active soluble rHSA protein, compared to soluble rHSA levels obtained without expression of molecular chaperone under said conditions.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Example 1

Materials and Methods
Bacterial Strains and Plasmids:

The E. coli host strain selected for expression of recombinant proteins in the present invention was E. coli origami2 DE3 (Cat No: 70956 Novagen, Germany). The vectors used in the present invention were pETHSA and pTf16 (Cat no. 3340 Takara Bio Inc. Japan). The gene sequence coding for the human serum albumin (Gene ID: 213) was cloned into pET23b vector (Cat. No. 69746 Novagen, Germany) under the T7 lac promoter. The gene HSA (Gene ID: 213) was amplified from plasmid pGEMT-cDNAHSA (Cat No: HG10968-G Sinobiological Inc., China) by PCR flanked with restriction sites of the High Fidelity enzymes Nhe1-HF and Xho1 (Cat No.: R3131S and R0146S respectively, New England Biolabs, UK) included in the forward primer and the reverse primer (SEQ ID NO: 1 and SEQ ID NO: 2 respectively). The restriction site in the forward primer sequence is identified by GCTAGC, while the restriction site in the reverse primer sequence is identified by CTCGAG. The plasmid contains the selective marker for ampicillin resistance. Plasmid pTF16 (purchased from Takara Bio Inc. Japan) was the chaperone plasmid (Trigger factor) selected for the present invention and it contains the Trigger Factor (molecular chaperone) for co-expression with rHSA in E. coli. The chaperone gene is found downstream of the inducible araC promoter which is induced by L-Arabinose. The plasmid contains the selective marker for chloramphenicol resistance.

Growth Culture Medium for Autoinduction:

For culturing recombinant host cells, auto-inducing ZY medium consisting of 1% Casein Enzymatic hydrolysate (an enzymatic digest of casein); 0.5% Yeast extract medium; 5052 solution (Glucose-0.05%, Lactose-0.2%, Glycerol—0.5%); NPS Buffer [Na2HPO4 (25 mM), KH2PO4 (25 mM); NH4Cl (50 mM)]; and 1 mM MgSO4, was selected.

Cell Lysis and Fractionation:

Normalized (for cross comparison, equal number of cells were taken based on O.D. reading) volumes of cell suspension, on the basis of number of cells per unit volume were harvested and centrifuged at 6000 rpm at 4° C. for 15-20 minutes. The cell pellet was resuspended in 10 mL of cold cell lysis buffer pH 7.4 (20-100 mMTris, 200-500 mMNaCl, 2-20 mM $MgCl_2$, 1-2 mMdithiothreitol, 5-20% glycerol, and 1-2 mMphenylmethanesulfonyl fluoride) and incubated in ice for 15-30 minutes. The resuspended cells were exposed to an ultrasonic cell disruptor to release the intracellular components in the lysis buffer. The sonicated cell lysate was centrifuged at 10,000 rpm for 45 min at 4° C. The supernatant was carefully aspirated without disturbing the pellet and the pellet was resuspended in equal volume of lysis buffer pH 7.4 (20-100 mMTris, 200-500 mM NaCl, 2-20 mM $MgCl_2$, 1-2 mMdithiothreitol, 5-20% glycerol, and 1-2 mMphenylmethanesulfonyl fluoride). The soluble fraction of the cell lysate was subsequently used for solubility analysis and for checking enzymatic activity of rHSA.

Solubility Analysis:

Amount of folded protein in a cell can be estimated based on the principle that proteins with a three dimensional structure are soluble in the cytoplasm and in aqueous buffers, whereas, denatured proteins are insoluble and occur as aggregates (Chaudhuri et al., Cell (2001); 107: 235-246). Thus, to estimate the extent of correct intracellular folding of rHSA, the induced cells were pelleted, resuspended in lysis buffer and lysed by sonication to release the intracellular components in the lysis buffer. The soluble components were separated from the insoluble mass by centrifugation of the cell lysate. The supernatant and the pellet were resuspended in the SDS loading buffer and analyzed by SDS-PAGE. The protein bands were visualized after staining with Coomassie Brilliant Blue R250. Relative quantity of the protein in soluble and pellet fractions was measured by selecting the whole cell extract band as reference band using the 'quantity tools' option of the analysis toolbox using Image Lab software in Bio-Rad Molecular Imager Gel Doc XR+ unit by densitometric analysis.

$$\text{Solubility (\%)} = \frac{rHSA\, Band\, intensity\, in\, soluble\, fraction\, of\, cell\, lysate}{rHSA\ Band\, intensity\, in\, the\, whole\, cell\, lysate} * 100$$

Activity Assay: HSA exhibits esterase like activity (Salvi et al., Drug metabolism and disposition (1997); 90-9556: 2504-0395). Esterase activity of the soluble of the cell lysate was carried out in a 1 mL reaction mixture at 25° C. containing 1 µM p-nitro phenyl acetate (pNPA, buffered with 50 mMTris, 50 mM NaCl, and 1 mM DTT, pH 7.4) as substrate for rHSA. The formation of p-nitrophenol was measured at wavelength of 410 nm spectrophotometrically after addition of normalized volume (equal number of cells per unit volume) of the cell lysate, having equal amount of total proteins estimated by Bradford's assay, in the reaction mixture and recorded every 5 seconds for 10 minutes using the kinetics/time application in DU 800 Beckman Coulter spectrophotometer. The slope (ΔC/Δt) which represents the rate of formation of the product (p-nitro phenol) was determined from the initial linear region of the curve. An extinction coefficient (c) of 18.3 mM$^{-1}$ cm$^{-1}$ was used for p-nitro phenol at 410 nm. Here, one unit activity of human serum albumin corresponds to 1 nmol of p-nitro phenol produced from p-nitro phenyl acetate per minute. Human serum albumin activity is expressed as nanomoles of pNP released/min/gram of dry cell weight.

$$EsteraseActivityofHSA = \frac{\left(\frac{\Delta C}{\Delta t} - \frac{\Delta C}{\Delta t}\text{blank}\right) * V_r * D * 1000}{\varepsilon * V_S * d}$$

Where:
(ΔC/Δt) is the slope of the activity assay curve in mM/min at 410 nm
(ΔC/Δt blank) is the slope of the activity assay curve in absence of enzyme in mM/min at 410 nm
ε is the extinction coefficient of p-nitrophenol in mM$^{-1}$ cm$^{-1}$
$V_r$ is the reaction mixture volume in mL
Vs is the volume of cell lysate used in mL
D is the correlation between OD$_{600nm}$ and cell dry weight in per g DCW
d is the path length in cm Example 2

Cloning of Human Serum Albumin (HSA) Gene in *E. coli* Cells

Mature 1.8 kb long HSA gene was amplified from plasmid pGEMT-cDNAHSA using primers having sequence as set forth in SEQ ID NO: 1 (forward primer), and SEQ ID NO: 2 (reverse primer) respectively, which was used as the parental template for sub cloning into the pET23b vector. Gradient PCR was carried out between 50° C. to 60° C. to determine the optimal annealing temperature which was found to be at 55° C. Further, the insert (HSA gene) and vector (pET23b) were double digested with the restriction enzymes NheI-HF and XhoI enzymes at 37° C. for 2 hours. The digestion of the vector was confirmed using agarose gel electrophoresis; the double digested HSA gene insert and pET23b vector DNA were extracted from the agarose gel by using the gel extraction kit (Cat No: 28704, Qiagen, USA). The ligation was carried out with the digested vector pET23b and digested HSA insert in the presence of T4 ligase enzyme at 16° C. for 16-18 hours and the resulting recombinant plasmid construct after ligation was designated as pETHSA.

The ligation mixture containing pETHSA plasmid was transformed into competent *E. coli* DH5a cells and plated on LB-Amp (conc. 50-100 μg/mL). The colonies that appeared on the plate after overnight incubation at 37° C. were isolated and transferred to 5 mL sterile LB media followed by overnight incubation at 37° C. The plasmid pETHSA was extracted from the cell culture by conventional plasmid DNA isolation techniques.

To develop the co-expression system, co-transformation of *E. coli* Origami 2 (DE3) competent cells with mixture of pETHSA and pTF16 plasmid [carrying the chloramphenicol (20-40 μg/mL) antibiotic resistance gene] was carried out by heat shock treatment according to standard molecular cloning protocols described in "Molecular Cloning: A Laboratory Manual" (by Sambrook T and Russell D, Cold Spring Harbor Laboratory Press, 2000.

Example 3

Co-Expression of Human Serum Albumin and Molecular Chaperone in *E. Coli* Cells

Figure 1B:
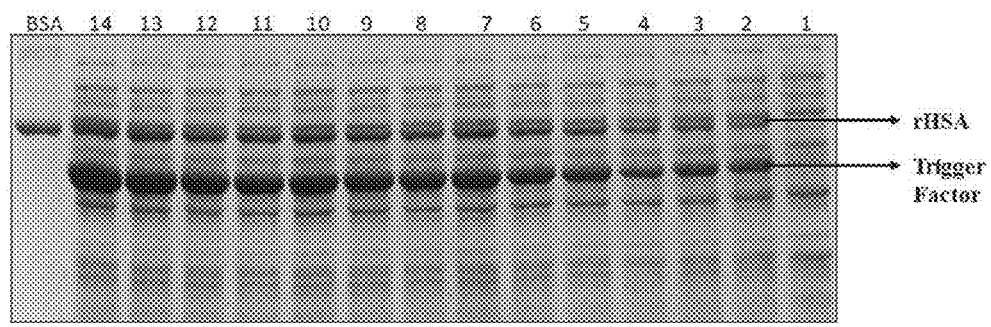
Figure 1C:
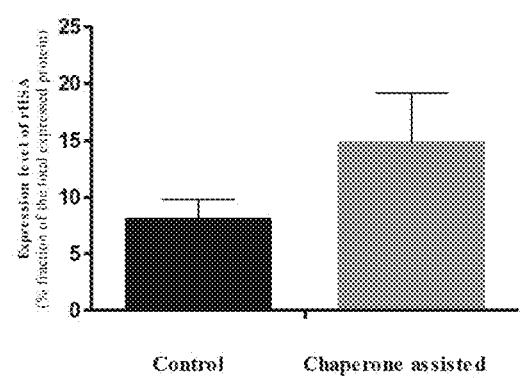

The co-transformed cells were grown and maintained under ampicillin (100-300 ug/mL) and chloramphenicol (20-40 ug/mL) selection pressure in the auto-induction medium at 37° C. Samples of the culture were taken and time points assessed included 1 h, 2 h, 3 h, 4 h, 6 h, 8 h, 10 h, 12 h, 14 h, 16 h and 20 h, to test the expression of rHSA in the absence of the trigger factor (molecular chaperone) (FIG. 1a). Additionally, the inducer of Trigger factor, L-Arabinose (0.3-0.6 mg/ml) was added to the culture medium to induce the expression of the Trigger factor (molecular chaperone) and samples were collected at 1 h, 2 h, 3 h, 4 h, 5 h, 6 h, 7 h, 8 h, 10 h, 12 h, 14 h, 16 h and 20 h (FIG. 1b), In addition, several experiments were undertaken (uninduced control) with uninduced culture medium (without the addition of L-Arabinose) for expression rHSA. BSA was used a standard marker. The expression of the recombinant rHSA and Trigger factor (molecular chaperone), together in the recombinant *E. coli* cells was confirmed from the samples loaded on the SDS-PAGE gel (FIG. 1a-c). In addition, several molecular chaperones systems were checked for higher expression of rHSA in *E. coli* system and we identified that Trigger factor expression (induced by L-Arabinose) gave the best results as compared to other molecular chaperone systems.

The results depicted in the present disclosure demonstrate that the expression level of rHSA, when co-expressed along with Trigger factor (molecular chaperone induced by L-Arabinose) system, is approximately 14.0-20.0% of the total expressed protein. The expression level of rHSA was about 7-10% of the total expressed protein when Trigger factor was not co-expressed in the cells. This is 1.5-2.0 fold more as compared to expression of rHSA without the Trigger factor expression (chaperone assistance). Trigger factor (molecular chaperone) expression therefore helps not only as a chaperone but also enhances the expression of the rHSA in the *E. coli* cytosol.

Example 3

Extraction of Soluble and Functional rHSA Protein Using Osmolytes

Osmolytes directly impact the stability and solubility of proteins, and certain organic osmolytes also aid in protein folding and refolding and preventing protein aggregation. Thus, in order to reduce downstream losses, various osmolytes as part of the extraction process were tested.

Auto induced recombinant *E. coli* Origami2 were grown at 10-20° C., preferably 15-20° C., and harvested. The harvested cells were resuspended in lysis buffer pH 7.4 (20-100 mMTris, 200-500 mM NaCl, 2-20 mM MgCl$_2$, 1-2 mM dithiothreitol, 5-20% glycerol, and 1-2 mM phenyl methanesulfonyl fluoride) comprising various osmolytes such as trehalose, sucrose, sorbitol, mannitol, sodium citrate, betaine, and L-proline at varying concentrations ranging from 0.1-1.0 M. The various lysis buffers comprising osmolytes were tested for optimal extraction of rHSA. The best osmolyte identified from the above experiments was trehalose at a concentration of 0.5-1.0 M in the lysis buffer.

The cell lysate obtained after lysis step was fractionated and analyzed for solubility and activity assay.

Figure 2:
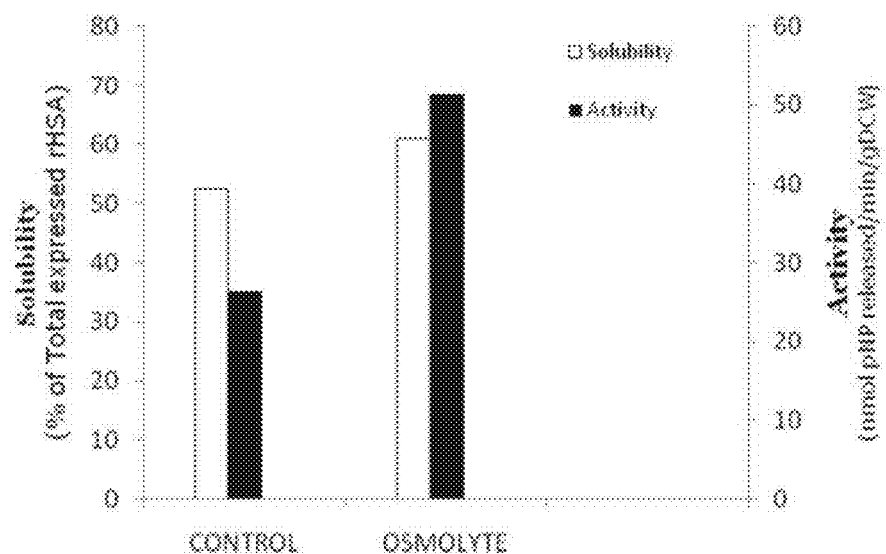
FIG. 2 shows the effect of osmolytes on the percent recovery and activity of soluble rHSA during expression and extraction, in accordance with an embodiment of the present disclosure.
Figure 3:
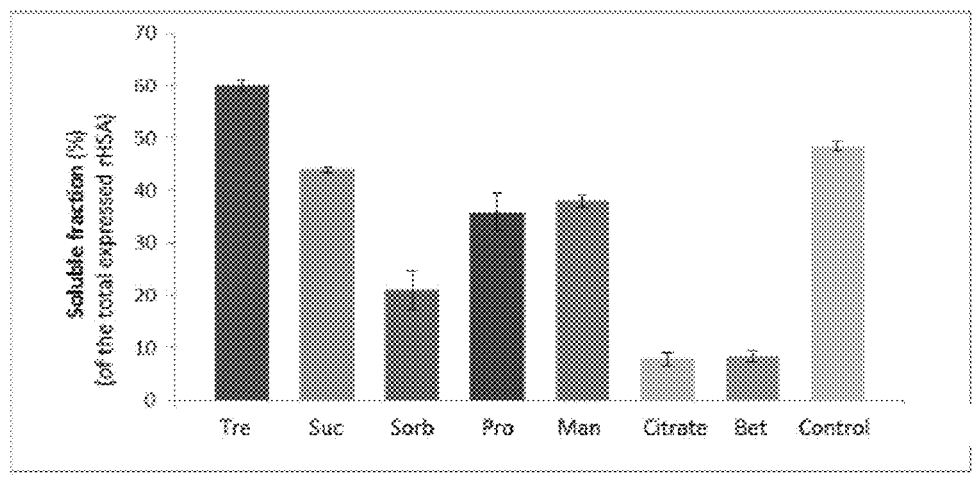
FIG. 3 shows the effect of different osmolytes during rHSA extraction on rHSA solubility, in accordance with an embodiment of the present disclosure.

As seen from FIGS. 2 and 3, when no osmolytes are used during the extraction step, about 50% of total expressed rHSA is obtained in the soluble fraction (control). Use of sucrose (Suc) at the concentration of 0.1-0.5M results in reduction of soluble fraction of rHSA (about 45%) compared to control. Use of sorbitol (Sorb) at the concentration of 0.1-0.5 M results in reduction of soluble fraction of rHSA (about 20%) compared to control. Use of proline (Pro) or mannitol (Man) at the concentration of 0.3-0.6 M results in reduction of soluble fraction of rHSA (about 35%) compared to control. Use of sodium citrate (Citrate) or betaine (Bet) at the concentration of 0.5-1.0 M results in reduction of soluble fraction of rHSA (about 10%) compared to control.

However, unexpectedly and surprisingly, it was observed that when trehalose (Tre) was used at the concentration of 0.5 to 1.0 M in the lysis step, there is a significant enhancement rHSA soluble fraction (60% compared to about 50% for control) (FIG. 3).

Figure 4:
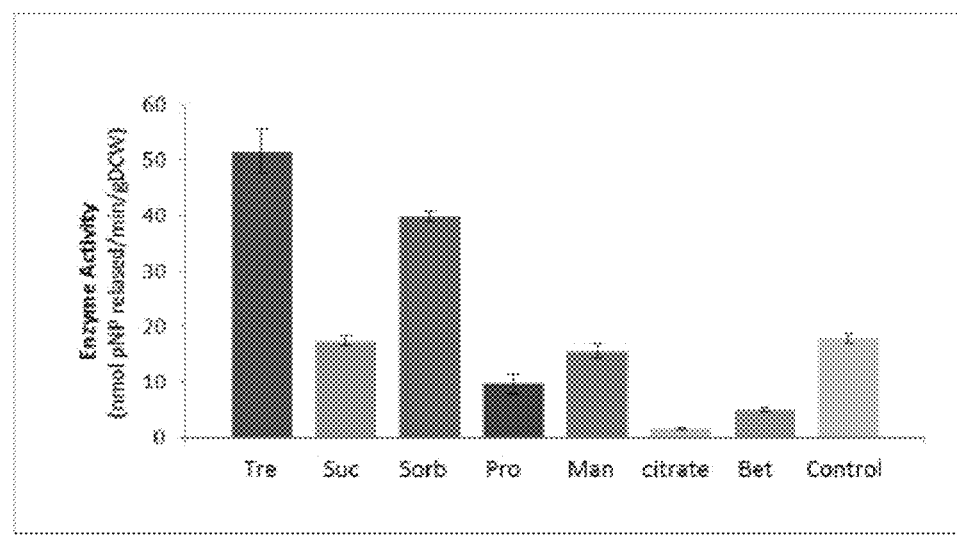
FIG. 4 shows the effect of different osmolytes during rHSA extraction on rHSA activity, in accordance with an embodiment of the present disclosure.

As seen in FIG. 4, when no osmolytes are used, the enzyme (rHSA) activity of the soluble fraction of rHSA is about 20 nmol pNP released/min/gDCW) (control). Use of sucrose (Suc) at the concentration of 0.1-0.5 M results in only a marginal reduction of soluble rHSA activity compared to control. Use of sorbitol (Sorb) at the concentration of 0.1-0.5 M results in an increase in soluble rHSA activity to about 40% compared to control. Use of proline (Pro) at the concentration of 0.3-0.6M results in a decrease in soluble rHSA activity to about 10% compared to control. Use of mannitol (Man) at the concentration of 0.3-0.6 M also results in a decrease in soluble rHSA activity to about 18% compared to control. Use of sodium citrate (Citrate) at the concentration of 0.-1M results in almost complete loss of soluble rHSA activity compared to control, while betaine (Bet) at the concentration of 0.5-1 M results in decrease in soluble rHSA activity to about 5% when compared to the control.

However, unexpectedly and surprisingly, it was observed that when trehalose (Tre) was used at the concentration of 0.5-1.0 M in the lysis buffer, a significant enhancement in soluble rHSA activity was observed (50% activity compared to about 20% in control) (FIG. 4).

Example 4

Improvement in the Expression Level and Cellular In Vivo Folding of the Recombinant HSA with the Assistance of Molecular Chaperone System Recombinant E. coli origami DE3 cells co-transformed with both the plasmids (pETHSA and pTF16) were inoculated in the primary culture of 5 mL LB medium containing both the antibiotics-ampicillin (100-300 µg/mL) and chloramphenicol (20-40 µg/mL). They were then inoculated from primary culture into a secondary culture in ZY auto-induction growth medium containing both ampicillin (100-300 µg/mL) and chloramphenicol (20-40 µg/mL) antibiotics. The secondary culture was grown at a temperature between 30-40° C. and the samples were collected and checked for optical density at regular time intervals. The growth of the cells was monitored and the cells were induced with L-Arabinose (Final conc. 0.3-0.6 mg/mL) when the $OD_{600}$ reached 0.2 to 0.5 (which took between 6-12 hours) and left to grow again until the $OD_{600}$ reached 0.6-1.0.

At this point, the incubation temperature of the recombinant host cell culture was lowered to a temperature in the range of 10-20° C. and cells were harvested after 8-12 hours of induction.

In order to obtain the expressed protein, the cells were resuspended in the lysis buffer containing the osmolyte trehalose in the concentration range of 0.5-1.0M. Cell lysate was obtained after the lysis step using conventional means. To summarize the steps above briefly, induced E. coli Origami2 (DE3) cells expressing both the Trigger factor (chaperone) and rHSA were harvested and pelleted down by centrifugation. The cell pellet obtained was resuspended in cell lysis buffer and incubated for 15-30 minutes. The resuspended cells in lysis buffer were then exposed to an ultrasonic cell disruptor to release the intracellular components in the lysis buffer. The sonicated cell lysate was fractionated by high speed centrifugation. The supernatant containing soluble fraction of rHSA was carefully aspirated without disturbing the pellet which contained the insoluble aggregated fraction of rHSA. Cells were then fractionated and analyzed for solubility and activity assay and was compared with the rHSA production in E. coli without Trigger factor expression (chaperone assistance).

Figure 5:
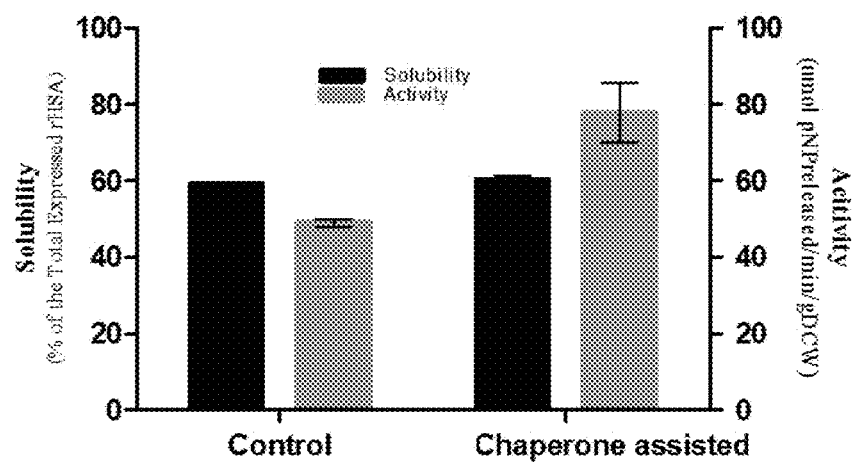
FIG. 5 shows the effect of chaperone assistance on solubility and activity of rHSA expressed in *E. coli* Origami2 (DE3), in accordance with the present disclosure.

Overall, the present disclosure provides a process for obtaining soluble and functional rHSA protein, in the presence of the molecular chaperone Trigger Factor. The process results in 1.5-2.0 fold increase in expression level of rHSA protein as compared to protein levels obtained without the presence of the molecular chaperone. Further, it is observed that though the soluble fraction of the rHSA expressed in the E. coli remains same in both the conditions (with or without chaperone assistance) i.e. 60%, there exists marked difference in the activity of the soluble fraction's functional content (FIG. 5). As has been demonstrated, the present process leads to 20-30% increase in functionally active soluble rHSA protein in the soluble fraction of rHSA when co-expressed along with the molecular chaperones as compared to when expressed alone in the E. coli host system (Recently filed patent application, IP no. 201611027096).

The enhancement in the activity is credited to the employment of trigger factor system for rHSA production as Trigger factor (molecular chaperone) acts to prevent misfolding and aggregation reaction by transiently shielding the hydrophobic regions exposed in non-native polypeptides during and after translation. (Agashe et al., Cell (2009); 117:199-209).

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

What is claimed is:

1. A process for production of soluble recombinant human serum albumin (rHSA) comprising:
   a) Obtaining recombinant *E. coli* host cells capable of co-expressing rHSA and L-Arabinose-inducible Trigger factor (molecular chaperone);
   b) culturing a culture comprising said recombinant *E. coli* host cells in an auto-induction culture medium at a first temperature in a first temperature range of 30-40° C. and for a time period of 6-12 hours until said culture reaches a first OD600 value in a first OD600 range of 0.2 to 0.5;
   c) Inducing Trigger factor by adding L-Arabinose to the auto-induction culture medium in the culture of b) at a concentration in a concentration range of 0.3 to 0.6 mg/ml to obtain an L-Arabinose-induced culture;
   d) culturing the L-Arabinose-induced culture of c) at said first temperature in the first temperature range of 30-40° C. until said L-Arabinose-induced culture reaches a second OD600 value in a second OD600 range of 0.6-1.0;
   e) Subsequent to d), culturing the L-Arabinose-induced culture at a second temperature in a second temperature range of 10-20° C. for a period of 8 to 10 hours;
   f) subsequent to e), harvesting the recombinant *E. coli* host cells from the L-Arabinose-induced culture to obtain harvested recombinant *E. coli* host cells; and
   g) re-suspending the harvested recombinant *E. coli* host cells in a lysis buffer comprising osmolytes in an osmolyte concentration range of 0.1 to 1.0 M where the osmolyte is selected from the group consisting of a trehalose, sucrose, sorbitol, mannitol, sodium citrate, betaine, L-proline or a combination thereof, and incubating said re-suspended cells for 15-30 minutes; and
   h) subsequent to g), sonicating the re-suspended cells to obtain a cell lysate;
   i) centrifuging said cell lysate to obtain therefrom a supernatant fraction; and
   j) extracting rHSA from the supernatant fraction to obtain soluble rHSA;
      wherein said process results in 20-30% increase in functionally active soluble rHSA protein, compared to soluble rHSA levels obtained from said recombinant *E. coli* host cells processed according to steps a), b) and d) through g) but without said step c) of inducing Trigger factor by adding L-Arabinose.

2. The process of claim 1, wherein said recombinant host cell is *E. coli* Origami2 (DE3).

3. The process of claim 1, wherein said auto-induction medium is ZY medium comprising ampicillin and chloramphenicol.

4. The process of claim 1, wherein said process results in 1.5-2.0-fold increase in an expression level of rHSA protein, compared to the expression level of rHSA protein that is obtained without L-Arabinose-induced expression of Trigger factor.

5. The method of claim 1, wherein said osmolytes is trehalose.

6. The method of claim 1, wherein the osmolytes are present at a concentration of 0.5-1.0M.

7. A method for producing recombinant human serum albumin (rHSA) comprising:
   a) obtaining recombinant *E. coli* Origami2 (DE3) cells comprising a plasmid capable of expressing rHSA and a plasmid pTf16 capable of expressing L-Arabinose-inducible Trigger factor (molecular chaperone);
   b) culturing a culture comprising said recombinant *E. coli* Origami2 (DE3) host cells in ZY medium comprising ampicillin and chloramphenicol, at a first temperature in a first temperature range of 30-40° C. and for a time period of 6-12 hours until the culture reaches a first $OD_{600}$ value in a first $OD_{600}$ range of 0.2 to 0.5;
   c) inducing Trigger factor by adding L-Arabinose to the ZY medium in the culture of b) at a concentration in a concentration range of 0.3 to 0.6 mg/ml to obtain an L-Arabinose-induced culture;
   d) culturing the L-Arabinose-induced culture of c) at said first temperature in the first temperature range of 30-40° C. until said L-Arabinose-induced culture reaches a second $OD_{600}$ value in a second $OD_{600}$ range of 0.6-1.0;
   e) subsequent to d), culturing the L-Arabinose-induced culture at a second temperature in a second temperature range of 10-20° C. for a period of 8 to 10 hours;
   f) subsequent to e), harvesting the recombinant *E. coli* host cells from the L-Arabinose-induced culture to obtain harvested recombinant *E. coli* host cells;
   g) resuspending the harvested recombinant *E. coli* host cells in a lysis buffer comprising trehalose in a trehalose concentration range of 0.5 to 1.0 M to obtain resuspended cells and incubating said resuspended cells for 15-30 minutes;
   h) subsequent to g), sonicating the resuspended cells to obtain a cell lysate;
   i) centrifuging said cell lysate to obtain therefrom a supernatant fraction; and j) extracting rHSA from the supernatant fraction to obtain soluble rHSA;

wherein said process results in a 1.5-2.0-fold increase in rHSA soluble protein levels and a 20-30% increase in functionally active soluble rHSA protein, compared to soluble rHSA levels obtained from said recombinant *E. coli* host cells processed according to steps a), b) and d) through j) but without said step c) of inducing Trigger factor by adding L-Arabinose.

* * * * *

UNITED STATES PATENT AND TRADEMARK OFFICE
CERTIFICATE OF CORRECTION

Page 1 of 1

PATENT NO. : 10,301,373 B2
APPLICATION NO. : 15/588379
DATED : May 28, 2019
INVENTOR(S) : Tapan Kumar Chaudhuri et al.

It is certified that error appears in the above-identified patent and that said Letters Patent is hereby corrected as shown below:

In the Claims

Column 15, Claim 1, Line 30:
"first OD600 value in a first OD600 range"
Should read:
--first $OD_{600}$ value in a first $OD_{600}$ range--.

Column 15, Claim 1, Line 39:
"second OD600 value in a second OD600 range"
Should read:
--second $OD_{600}$ value in a second $OD_{600}$ range--.

Signed and Sealed this
Twenty-fourth Day of December, 2019

Andrei Iancu
*Director of the United States Patent and Trademark Office*

SEQUENCE LISTING

<160> NUMBER OF SEQ ID NOS: 2

<210> SEQ ID NO 1
<211> LENGTH: 28
<212> TYPE: DNA
<213> ORGANISM: artificial sequence

```
<220> FEATURE:
<223> OTHER INFORMATION: forward primer to amplify HSA

<400> SEQUENCE: 1
aaagctagca tggatgcaca caagagtg                                             28

<210> SEQ ID NO 2
<211> LENGTH: 24
<212> TYPE: DNA
<213> ORGANISM: artificial sequence
<220> FEATURE:
<223> OTHER INFORMATION: reverse primer to amplify HSA

<400> SEQUENCE: 2
ggactcgagt aagcctaagg cagc                                                 24
```